US009818394B2

(12) United States Patent
Fuller

(10) Patent No.: US 9,818,394 B2
(45) Date of Patent: Nov. 14, 2017

(54) REALISATION OF CONTROLLER TRANSFER FUNCTION FOR ACTIVE NOISE CANCELLATION

(76) Inventor: Graeme Colin Fuller, Auckland (NZ)

( * ) Notice: Subject to any disclaimer, the term of this patent is extended or adjusted under 35 U.S.C. 154(b) by 179 days.

(21) Appl. No.: 12/956,200

(22) Filed: Nov. 30, 2010

(65) Prior Publication Data

US 2011/0211707 A1 Sep. 1, 2011

Related U.S. Application Data

(60) Provisional application No. 61/264,995, filed on Nov. 30, 2009.

(51) Int. Cl.
*A61F 11/06* (2006.01)
*G10K 11/178* (2006.01)

(52) U.S. Cl.
CPC .. *G10K 11/1782* (2013.01); *G10K 2210/3028* (2013.01); *G10K 2210/3056* (2013.01)

(58) Field of Classification Search
CPC .............. H04R 1/1083; H04R 2460/01; G10K 2210/1081; G10L 21/0208
USPC ............ 381/71.1, 71.14, 99, 101, 102, 71.6, 381/94.1–94.3, 98, 103, 317–318
See application file for complete search history.

(56) References Cited

U.S. PATENT DOCUMENTS

| | | | |
|---|---|---|---|
| 1,368,307 | A | 2/1921 | Waldron |
| 1,498,727 | A | 6/1924 | Haskel |
| 1,514,152 | A | 11/1924 | Gemsback |
| 1,586,140 | A | 5/1926 | Bonnette |
| 1,807,225 | A | 5/1931 | Pack |
| 2,346,395 | A | 4/1944 | Rettinger |
| 2,379,891 | A | 7/1945 | Eckardt |
| 2,427,844 | A | 9/1947 | Eklov |
| 2,490,466 | A | 12/1949 | Olson |
| 2,603,724 | A | 7/1952 | Kettler |
| 2,622,159 | A | 12/1952 | Herman . |
| 2,714,134 | A | 7/1955 | Touger |
| 2,761,912 | A | 9/1956 | Touger |
| 2,775,309 | A | 12/1956 | Villchur |
| 2,848,560 | A | 8/1958 | Wiegand |

(Continued)

FOREIGN PATENT DOCUMENTS

| | | |
|---|---|---|
| CN | 1101203 | 4/1995 |
| CN | 1213626 | 4/1999 |

(Continued)

OTHER PUBLICATIONS

Keen, R.G. "Simple, Easy Parametric and Graphic EQ's, Plus Peaks and Notches." 1999. <http://www.geofex.com/article_folders/eqs/paramet.htm>.*

(Continued)

*Primary Examiner* — Joseph Saunders, Jr.
*Assistant Examiner* — James Mooney
(74) *Attorney, Agent, or Firm* — Jackson Walker LLP

(57) ABSTRACT

An apparatus for realizing an active noise cancellation control law transfer function between a sensing microphone and a speaker. The apparatus includes a multiplicity of filters. Each filter is operable over a different frequency range. At least one filter has an adjustable parameter whereby the filter can be adjusted such that the filters cumulatively realize a required control law transfer function. The adjustable parameter may in one embodiment be the amplitude. In other embodiments, it may be other parameters.

27 Claims, 4 Drawing Sheets

(56) References Cited

U.S. PATENT DOCUMENTS

Figure 1:
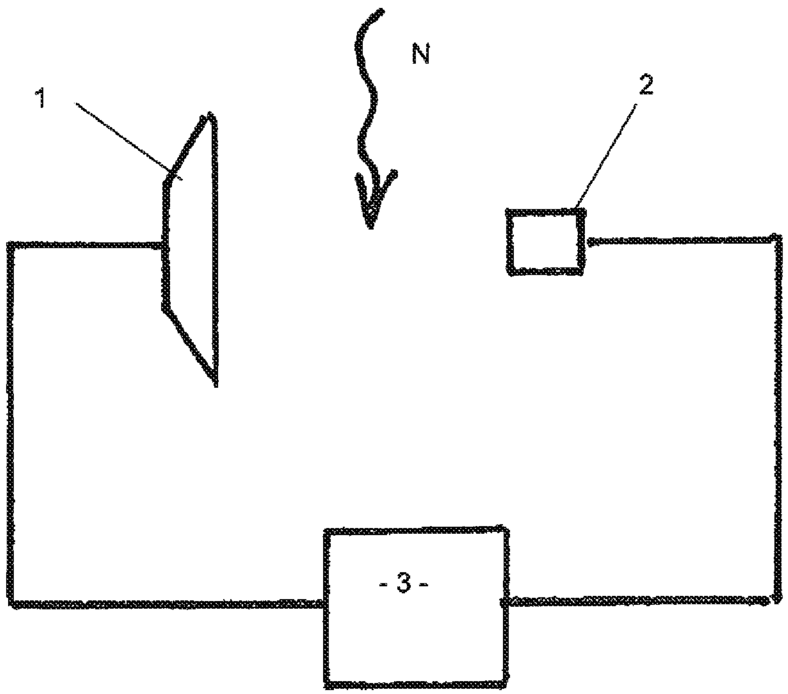

| | | | |
|---|---|---|---|
| 2,972,018 A | 2/1961 | Hawley et al. | |
| 2,989,598 A | 6/1961 | Touger | |
| 3,073,411 A | 1/1963 | Bleazey | |
| 3,112,005 A | 11/1963 | Shaw | |
| RE26,030 E | 5/1966 | Marchand | |
| 3,367,040 A | 2/1968 | Vani | |
| 3,403,235 A | 9/1968 | Bishop | |
| 3,532,837 A | 10/1970 | Dyar | |
| 3,602,329 A | 8/1971 | Bauer et al. | |
| 3,644,939 A | 2/1972 | Beguin | |
| 3,727,004 A | 4/1973 | Bose | |
| 3,766,332 A | 10/1973 | Carlson | |
| 3,927,262 A | 12/1975 | Goeckel | |
| 3,997,739 A | 12/1976 | Kishikawa | |
| 4,005,267 A | 1/1977 | Gorike | |
| 4,005,278 A | 1/1977 | Gorike | |
| 4,006,318 A | 2/1977 | Sebesta | |
| 4,027,117 A | 5/1977 | Nakamura | |
| 4,041,256 A | 8/1977 | Ohta | |
| 4,058,688 A | 11/1977 | Nishimura | |
| 4,156,118 A | 5/1979 | Hargrave | |
| 4,158,753 A | 6/1979 | Gorike | |
| 4,211,898 A | 7/1980 | Atoji et al. | |
| 4,297,537 A | 10/1981 | Babb | |
| 4,338,489 A | 7/1982 | Gorike | |
| 4,347,405 A | 8/1982 | Davis | |
| 4,399,334 A | 8/1983 | Kakiuchi | |
| 4,403,120 A | 9/1983 | Yoshimi | |
| 4,418,248 A | 11/1983 | Mathis | |
| 4,441,576 A | 4/1984 | Allen | |
| 4,455,675 A | 6/1984 | Bose | |
| 4,494,074 A | 1/1985 | Bose | |
| 4,527,282 A | 7/1985 | Chaplin et al. | |
| 4,528,689 A | 7/1985 | Katz | |
| 4,529,058 A | 7/1985 | Emery | |
| 4,572,324 A | 2/1986 | Fidi et al. | |
| 4,581,496 A | 4/1986 | Sweany | |
| 4,592,366 A | 6/1986 | Sainomoto | |
| 4,644,581 A | 2/1987 | Sapiejewski | |
| 4,646,872 A | 3/1987 | Kamon | |
| 4,669,129 A | 6/1987 | Chance | |
| 4,670,733 A | 6/1987 | Bell | |
| 4,742,887 A | 5/1988 | Yamagishi | |
| 4,809,811 A | 3/1989 | Gorike | |
| 4,847,908 A | 7/1989 | Kieuwendijk | |
| 4,852,177 A | 7/1989 | Ambrose | |
| 4,893,695 A | 1/1990 | Tamura et al. | |
| 4,905,322 A | 3/1990 | Aileo et al. | |
| 4,922,542 A | 5/1990 | Sapiejewski | |
| 4,949,806 A | 8/1990 | Hofer | |
| 4,985,925 A | 1/1991 | Langberg et al. | |
| 4,989,271 A | 2/1991 | Sapiejewski | |
| 5,001,763 A | 3/1991 | Moseley | |
| 5,020,163 A | 6/1991 | Aileo et al. | |
| 5,117,461 A | 5/1992 | Moseley | |
| 5,134,659 A | 7/1992 | Moseley | |
| 5,181,252 A | 1/1993 | Sapiejewski | |
| 5,182,774 A | 1/1993 | Bourk | |
| 5,208,868 A | 5/1993 | Sapiejewski | |
| 5,267,321 A | 11/1993 | Langberg | |
| 5,305,387 A | 4/1994 | Sapiejewski | |
| 5,343,523 A | 8/1994 | Bartlett et al. | |
| 5,440,642 A | 8/1995 | Denenberg et al. | |
| 5,497,426 A | 3/1996 | Jay | |
| 5,504,281 A | 4/1996 | Whitney | |
| 5,604,813 A * | 2/1997 | Evans et al. | 381/71.6 |
| 5,652,799 A | 7/1997 | Ross et al. | |
| 5,668,883 A * | 9/1997 | Abe et al. | 381/72 |
| 5,675,658 A | 10/1997 | Brittain | |
| 5,740,257 A | 4/1998 | Marcus | |
| 5,913,178 A | 6/1999 | Olsson | |
| 5,937,070 A | 8/1999 | Todter et al. | |
| 5,970,160 A | 10/1999 | Nilsson et al. | |
| 6,061,456 A | 5/2000 | Andrea et al. | |
| 6,163,615 A | 12/2000 | Callahan | |
| 6,278,786 B1 | 8/2001 | McIntosh | |
| 6,597,792 B1 | 7/2003 | Sapiejewski | |
| 6,831,984 B2 | 12/2004 | Sapiejewski | |
| 7,103,188 B1 | 9/2006 | Jones | |
| 7,171,010 B2 * | 1/2007 | Martin et al. | 381/98 |
| 7,248,705 B1 | 7/2007 | Mishan | |
| 8,014,541 B1 * | 9/2011 | Abel et al. | 381/103 |
| 2002/0015501 A1 | 2/2002 | Sapiejewski | |
| 2005/0254564 A1 * | 11/2005 | Tsutsui | H03G 5/025 375/229 |
| 2008/0031471 A1 * | 2/2008 | Haulick et al. | 381/86 |

FOREIGN PATENT DOCUMENTS

| | | | |
|---|---|---|---|
| DE | 3512405 | A1 | 10/1985 |
| DE | 8703084 | | 11/1987 |
| EP | 0195641 | B1 | 9/1986 |
| EP | 0582404 | | 2/1994 |
| EP | 0582404 | A3 | 2/1994 |
| EP | 0414479 | | 9/1995 |
| EP | 0688143 | | 12/1995 |
| EP | 0873040 | | 10/1998 |
| EP | 0688143 | B1 | 8/2001 |
| FR | 2595178 | A1 | 9/1987 |
| GB | 1379372 | | 1/1975 |
| GB | 2000941 | | 1/1979 |
| GB | 2168220 | A | 6/1986 |
| GB | 2172470 | A | 9/1986 |
| GB | 2187361 | A | 9/1987 |
| GB | 2188210 | A | 9/1987 |
| GB | 3706481 | C2 | 9/1987 |
| GB | 2234882 | | 2/1991 |
| GB | 2234882 | A | 2/1991 |
| JP | 04227396 | A | 8/1992 |
| NL | 8101815 | | 11/1981 |
| WO | WO91/13429 | | 9/1991 |
| WO | WO 95/00946 | | 1/1995 |
| WO | WO 95/08907 | | 3/1995 |
| WO | WO 98/41974 | | 9/1998 |
| WO | 2008-090342 | A2 | 7/2008 |
| WO | 2010-049241 | A1 | 5/2010 |

OTHER PUBLICATIONS

"Q107 State Variable Filter." Synthesizers.com. N.p., Oct. 13, 2004. Web. <http://www.synthesizers.com/q107.html>.*

Audio Technica / ATH-ANC7 Bode Plot, unknown author, submitted with IDS dated Sep. 5, 2017.*

Maxell / HP-NC22 Bode Plot, unknown author, submitted with IDS dated Sep. 5, 2017.*

D'Appolito Testing Loudspeakers, Audio Amateur Publications, 1998, Chapter 2, Driver Testing, pp. 9-36.

Beranek, Noise and Vibration Control, Chapter 10, pp. 245-269.

John Borwick, Loudspeaker and Headphone Handbook (1st Ed., Butter & Co., 1988) complete text including references cited therein.

Small, Richard H., "Closed-Box Loudspeaker Systems", Part 1: Analysis, Journal of the Audio Engineering Society, 1972, pp. 271-282.

E.A.G. Shaw & G.J. Thiessen, Acoustics of Circumural Earphones, 34 The Journal of the Acoustical Society of America, No. 9, Sep. 1962.

Alfred DiMattia, "A Practical Ear Enclosure With Selectively Coupled Volume", AES Paper No. 460, AES Convention 31 (Oct. 1966), pp. 1-12.

Alfred DiMattia, "A Practical Ear EncicisureWith Selectively Coupled Volume", vol. 15 The Jounal of the Acoustical Society of America, No. 3 (Jul. 1967), pp. 295-298.

Naraji Sakamoto, "Linear-Drive Headphones with Eardrum Response", AES Paper 1341, AES Convention 60 (May 1978), pp. 1-32.

Carl Poldy, "The Electrical Equivalent Circuit of Porous Complaint Membranes and Related Systems", AES Paper 1957 (D2), AES Convention 73 (Mar 1983), pp. 1-15.

(56) References Cited

OTHER PUBLICATIONS

Ver, et al., “Sound-Absorbing Materials and Sound Absorbers”, Noise and Vibration Control Engineering (John Wiley & Sons, Inc.2006), pp. 215-277.
Borwick, Loudspeaker and Headphone Handbook, Third Edition, Focal Press, Section 14.2.7 and. 14.2.8.
Borwick, Loudspeaker and Headphone Handbook Third Edition, Focal Press, Section 14.2.3 and Fig. 14.8 and p. 605.
Beranek, et al., Noise and Vibration Control Engineering, Second Edition (John Wiley & Sons, Inc. 2006) p. 216 231-232, 235-239.
Handbook for Sound Engineers; The New Audio Cyclopedia, Second Edition (Macmillan Computer Publishing, Copyright 1987 and 1991), p. 119.
Small, Richard H., “Direct-Radiator Loudspeaker System Analysis”, IEEE Transactions on vol. 19, issue 4, Dec. 1971, pp. 269-281.
D’Appolito, “Low-Frequency System Electrical Impedance Tests,” Testing Loudspeakers, Chapter 3, pp. 37-49.
Allan D. Pierce, Acoustics (excerpt), Acoustical Society of America through the American. Institute of Physics, pp. 324-328.
Peter Lert, “Triumph of the Voyager,” Air Progress vol. 49, No. 3, Mar. 1987, pp. 6-12 and 75-77.
“Headset cancels noise with noise,” Show Daily, Jun. 15, 1987, p. 32.
E.H. Berger, “Using the NPR to Estimate the Real World Performance of Hearing Protection,” Sound and Vibration, Jan. 1983, pp. 12-18.
Alice H. Suter, “Noise Wars,” Technology Review, Nov./Dec. 1989, pp. 42-49.
George F. Kuhn, “The Pressure Transformation from a Diffuse Sound Field to the External Ear and . . . ,” J. Acoust. Soc. Am., vol. 65, No. 4, Apr. 1979, pp. 991-100.
Terrell, et al., “Predicting Noise Reduction from Absorptive Treatments . . . ,” American Industrial Hygiene Association Journal, vol. 44 Nov. 1983, pp. 809-813.
Jazef J. Zwislocki, “Sound Analysis in the Ear: A History of Discoveries,” American Scientist, vol. 69, Mar.-Apr. 1981, pp. 184-192.
Don Denton, “Program Converts Test Data into Reliability Numbers,” Electronic Design, Aug. 19, 1982, pp. 157-164.
Amar G. Bose, “Sound Recording and Reproduction . . . ” Technology Review, vol. 75, No, 7, Jun. 1973, and No. 8, Jul./Aug. 1973 by MIT, Cambridge, MA.
John Free, “Noise Zapper,” Popular Science, Jan. 1987, pp. 76-77 and 96.
Jack Norris, “Voyager, The World Flight, The Official Log, Flight Analysis and Narrative Explanation,” Northridge, California, ISBN 09620239-0-6 (1987).
“Bose Adoustic Noise Cancelling Headsets to be Tested on Voyager Flight,” Bose Press Release, Framingham, MA.
“Voyager Pilots Avoid Hearing Loss on Historic Flight, Bose Corporation’s Noise-Cancelling Headsets Were ‘Mission Critical,’” Bose News Release, Framingham, MA.
William D. Marbach, “Up, Up and Around,” Newsweek, Dec. 29, 1986, pp. 34-44.
Marc E. Cook, “The Art of Noise,” AOPA Pilot, Dec. 1989, pp. 65-69.
Phil Todd, “Principles of Magnetic Component Design,” Powercon10 Professional Advancement Seminar, Power Innovations, Mar. 21, 1983, San Diego, California. pp. 1-35.
Capt. Stephen P. Shelton, “Active Noise Reduction (ANR),” Article (publication information unknown).
McKinley, et al., “Estimated Reductions in Noise-Induced Hearing Loss by Application of ANR Headsets,” Scientific Basis of Noise-Induced Hearing Loss, Thieme, Chapter 28.
“Noise-Cancelling Headsets Featured at Telex Booth,” NBAA Convention News, New Orleans, LA, Sep. 30, 1987, pp. 85-86.
Telex Communications, Inc. Aviation Products and Price Information Sheet, Effective Date Nov. 15, 1986.
“Anti-Lawaai Koptelefoon Van Sony” Article (publication information unknown).
“MDR-NC20 Service Manual,” Noise Canceling Stereo Headphones Sony.
“MDR-NC10 Service Manual,” Noise Canceling Stereo Headphones Sony.
“Presenting Sennheiser Electronic,” Sennheiser Chronicle, Sennheiser Electronic, D-3002 Wedemark.
“Aearo Peltor Stratospher,” AOPA Pilot, Jul. 1998, p. 114.
“Active Noise Reduction for use in Aircraft” Helmets Limited, Apr. 1990.
“Creative Unveils Aurvana X-Fi Noise-Canceling Headphones,” Wireless News, Sep. 24, 2007 M2 Communications Ltd.
David Clark Company, Inc. Noise Attenuating Aviation Headsets and Accessories Product Information Sheet, 8 pages.
David Pogue, “Flying? Sit Back and Relax—And Zone Out for Less; Competing with Noise-Canceling Bose Headgear.(Finance),” International Herald Tribune, Jun. 14, 2007: 1-2.
Audio-Technica 900 Series Stereo Headphones Product Information Sheet, 2 pages.
Elliott H. Berger, “Single Number Measures of Hearing Protector Noise Reduction,” E-A-R LOG2 (1996).
Elliott H. Berger, “Preferred Methods for Measuring Hearing Protector Attenuation,” The 2005 Congress and Exposition on Noise Control Engineering, Aug. 7-10, 2005, Brazil.
Gauger, et al., “Voyager Pilots Avoid Hearing Loss on Historic Flight,” S)V Observer, Bose Corporation, Framingham, MA.
Samuel Gilman, “Some Factors Affecting the Performance of Airline Entertainment Headsets,” Journal of Audio Engineering Society, vol. 31, No. 12, Dec. 1983: pp. 914-920.
Don E. Bray, “Turbulent-Boundary-Layer Noise in the Interior of Aircraft Operating . . . ,” Journal of Acoustical Society of America, vol. 60, No. 5, Nov. 1976: 1223-1225.
“Uniroyal Expanded Products Technical Bulletin Data,” Uniroyal, Inc., Mishawaka, Indiana, Jul. 1982.
“More ANR from Bose, LightSPEED and DRE,” The Aviation Consumer, Sep. 1998, p. 14.
“The Bose Acoustic Noise Cancelling Headset System,” Bose Corporation, Framingham, MA, coypright 1987 Bose Corporation.
Dick Weeghman, “Headset Survey Results,” The Aviation Consumer. Greenwich, CT, Aug. 1, 1991.
Fred Mackerodt, “Aviation Sounds of Silence,” Popular Mechanics, vol. 167, No. 3, Mar. 1990.
Michael Alexander, “Bose Corp. Cuts Niche in Specialty Audio Market,” The Boston Globe, Boston MA, Nov. 20, 1987.
Kenneth Korane, “Thermoplastic polyurethane extends headset life,” News Off the Wire, Jul. 8, 1999.
David Clark Noise Attenuating Headsets Product Information, 11 pages, copyrighted 1989 David Clark Company.
K. Takagi, et al., “Prediction of Noise-Induced Temporary Threshold Shift,” Journal of Sound and Vibration, Academic Press Limited (1988), pp. 513-519.
Kreul, et al., “Factors Affecting Speech Discrimination Test Difficulty,” Stanford Research Institute, Menlo Park, California (7 pages).
Juergan Schroeter, “The Use of Acoustical Test Fixtures for the Measurement of Hearing . . . Part I . . . ” J. Acoust. Soc. Am., Apr. 1986, vol. 79, No. 4, pp. 1065-1081.
Juergan Schroeter et al., “The Use of Acoustical Test Fixtures for the Measurement of Hearing . . . Part II . . . ” J. Acoust. Soc. Am., Aug. 1986, vol. 80, No. 2, pp. 505-527.
E.H. Berger, “Method of Measuring the Attenuation of Hearing Protection Devices,” J. Acoust. Soc. Am., Jun. 1986, vol. 79, No. 6, pp. 1655-1687.
Berger, et al., “Development of a New Standard Laboratory Protocol . . . Part III . . . ” J. Acoust. Soc. Am., Feb. 1998, vol. 103; No. 2, pp. 665-672.
Berger, et al., “Influence of Physiological Noise and the Occlusion Effect . . . ” J. Acoust. Soc. Am. Jul. 1983, vol. 74, No. 1, pp. 81-94.
Karl D. Kryter, “Methods for the Calculation and Use of the Articulation Index,” J. Acoust. Soc. Am., Nov. 1962, vol. 34, No. 11, pp. 1689-1697.
Casali, et al., “Communications Headset Augmentation Via Active Noise Cancellation . . . ” Proceedings of the Human Factors and Ergonomics Society 37th Annual Meeting—1993: 554-58.

(56) References Cited

OTHER PUBLICATIONS

"American National Standard Methods for the Calculation of the Articulation Index" American National Standards Institute, Inc., ANSI S3.5-1969: 6-24.
Stephen Elliott, "Down with Noise," IEEE Spectrum Jun. 1999, pp. 54-61.
Larry J. Eriksson, "A Brief Social History of Active Sound Control," Sound and Vibration, Jul. 1999, pp. 14-17.
Vaudrey, et al., "A Comparison of ANR Headset Performance for Loopshaping . . . " Presentation Brochure, Session 3aSP, 136th Meeting—Acoustical Society of America, Oct. 1998.
E. Zwicker, et al., "Critical Band Width in Loudness Summation," J. Acoust. Soc. Am., May 1957, vol. 29, No. 5, pp. 548-557.
E. Zwicker, "Subdivision of the Audible Frequency Range into Critical Bands" J. Acoust. Soc. Am., Feb. 1961, vol. 33, No. 2, p. 248.
"Noise Canceling Headset System Undergoes Developmental Tests," Aviation Week & Space Technology, Nov. 24, 1986.
John Makhoul, "Linear Prediction: A Tutorial Review," Proceedings of the IEEE, vol. 63, No. 4, Apr. 1975, pp. 561-580.
Antila, Marko, Antti Kääriä, and Jari Kataja. "Experiments With Field Programmable Analog Arrays In Active Noise Control." in Forum Acusticum 2005. pp. 865-868 2005.
Clyne Media, Inc., "Audio-Technica Introduces ATH-ANC7 Quietpoint(TM) Active Noise-Cancelling Headphones" (Jan. 8, 2007).

* cited by examiner

REALISATION OF CONTROLLER TRANSFER FUNCTION FOR ACTIVE NOISE CANCELLATION

This application claims the benefit of, incorporates by reference, and priority from U.S. Provisional Patent Application Ser. No. 61/264,995, filed Nov. 30, 2009.

FIELD OF THE INVENTION

This invention relates to active noise cancellation systems, and has application to both feedback and feedforward control architectures, or combinations of these.

BACKGROUND

All active noise cancellation products, whether they are based on a feedback or feedforward control architecture (or a combination of these two architectures) require a tailored transfer function between the noise sensing device (typically one or more sensing microphones) and the device that creates the acoustic response required to cancel the sensed noise (typically a speaker). In this document the transfer function between the sensing microphone (s) and the speaker is referred to as the control law transfer function. This transfer function facilitates the realisation of noise cancellation over a suitable bandwidth whilst minimising noise amplification and/or instability outside this bandwidth.

Classically the control law transfer function has been realised through use of an analog filter which consists of a fixed combination of active and passive components. Such a realisation has the following disadvantages:

1. Its fixed nature does not allow adjustment of production variation within the electro-acoustics to which it interfaces.
2. its fixed nature does not allow easy accommodation of a range of electro-acoustic designs.
3. Its fixed nature does not permit dynamic adjustment of the control law to provide optimised noise cancellation based on the prevailing noise field.
4. The component count of the implementation is high and typically does not lend itself to integration within an integrated circuit.

OBJECT

It is an object of the present invention to provide a method or apparatus for realising an active noise cancellation control law transfer function which will ameliorate at least one of the foregoing disadvantages, or which, alternatively, will at least provide a useful alternative to existing solutions.

SUMMARY

In one aspect the disclosed subject matter provides apparatus for realising an active noise cancellation control law transfer function between a sensing microphone and a speaker, the apparatus including a plurality of filters, each filter being operable over a different frequency range, and at least one filter having at least one adjustable parameter whereby the filter can be adjusted such that the filters cumulatively realise a required control law transfer function.

Each filter may include at least one adjustable parameter. In some embodiments the adjustable parameter is amplitude. In other embodiments the adjustable parameter is bandwidth.

The adjustable filter may comprise a parametric filter.

In one embodiment the adjustable parameter is dynamically adjustable. An adjustment controller may be provided to adjust the adjustable parameter.

In another aspect the disclosed subject matter broadly provides a method of active noise cancellation for apparatus including a speaker and sensing microphone and a plurality of filters, each filter being operable over a different frequency range, and at least one filter having at least one adjustable parameter whereby the filter can be adjusted, the method including:

- determining one or more acoustic or electro-acoustic characteristics of the apparatus, and;
- adjusting the adjustable parameter dependent on the characteristic such that the filters cumulatively realise a control law transfer function to implement active noise cancellation.

In another aspect the disclosed subject matter broadly provides a method of active noise cancellation for apparatus including a speaker and sensing microphone and a plurality of filters, each filter being operable over a different frequency range, and at least one filter having at least one adjustable parameter whereby the filter can be adjusted, the method including:

- sensing the noise cancellation performance of the apparatus, and;
- adjusting the adjustable parameter dependent on the sensed performance such that the filters cumulatively realise a control law transfer function to implement active noise cancellation.

The method may further comprise dynamically adjusting the adjustable parameter.

Further aspects will become apparent from the following description.

BRIEF DRAWING DESCRIPTION

One or more embodiments of the invention will be described below with reference to the drawings in which:

FIG. 1: Is a diagrammatic representation of a known feedback active noise cancellation system.

Figure 2:
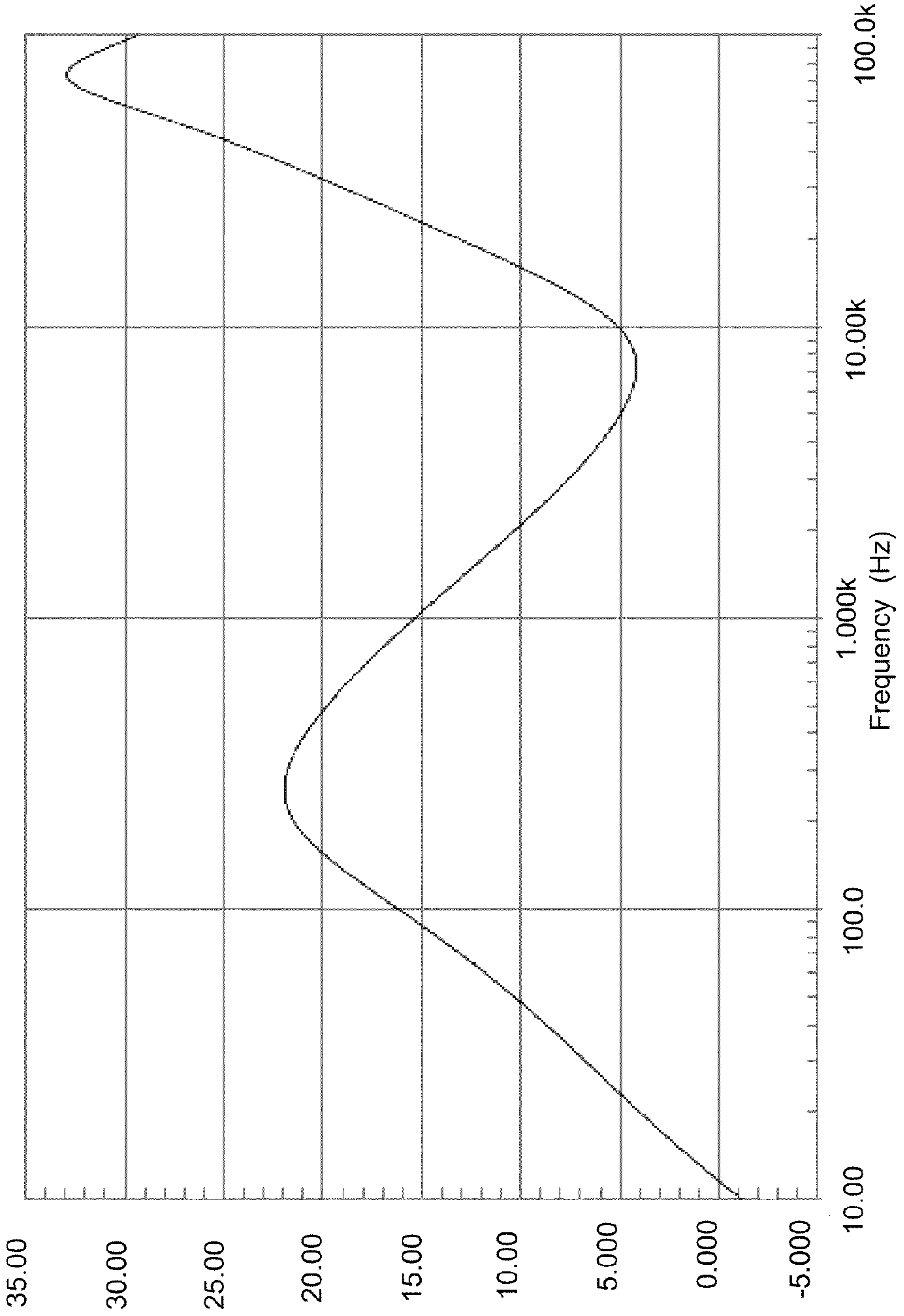

FIG. 2: Is a diagram showing gain plotted against frequency for the desired response for a known control law a transfer function for an active noise cancellation system such as that shown diagrammatically in FIG. 1

Figure 3:
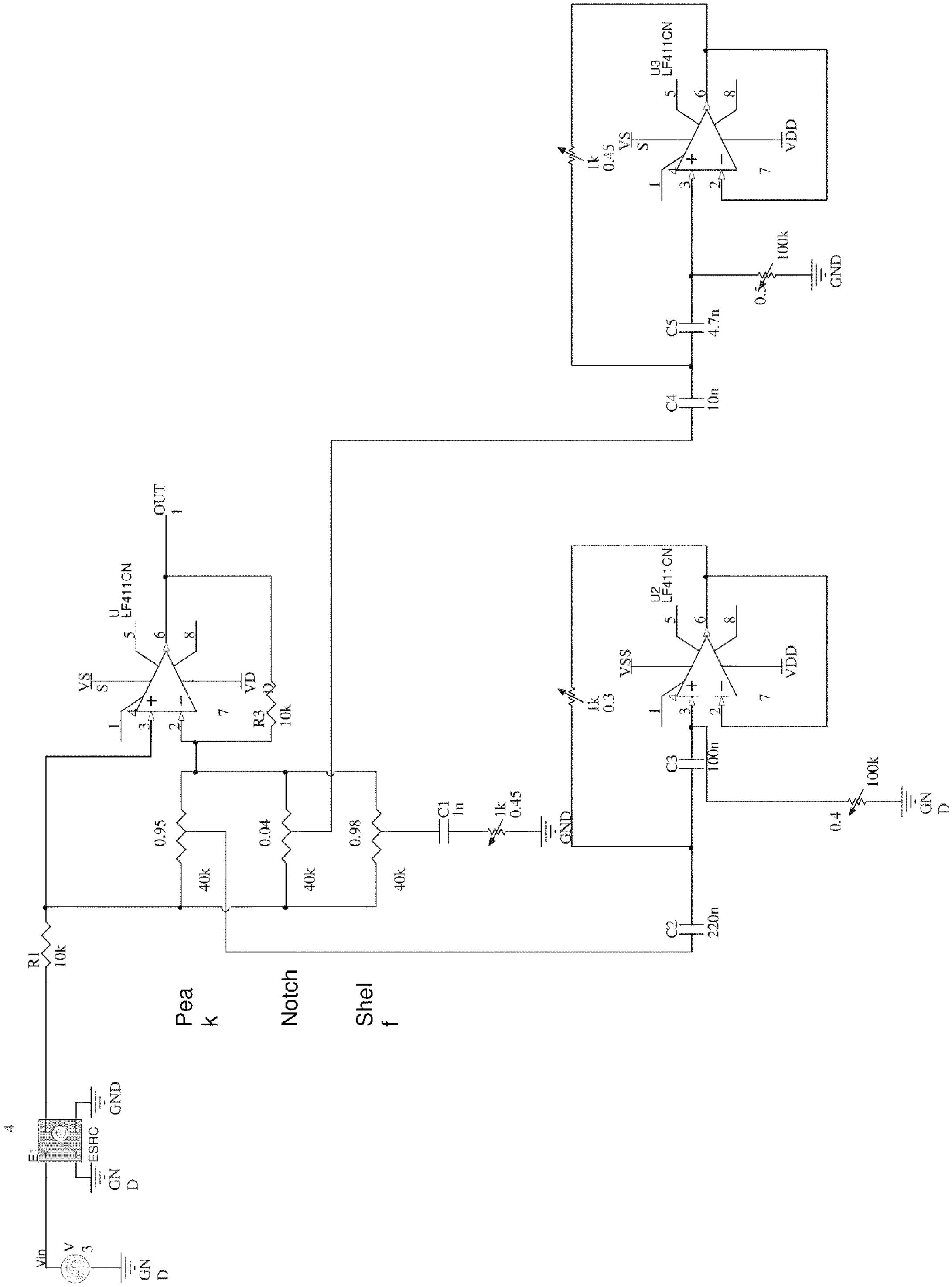

FIG. 3: Is a circuit diagram showing one example of a possible circuit realisation of a control law transfer function such as that represented in FIG. 2.

Figure 4:
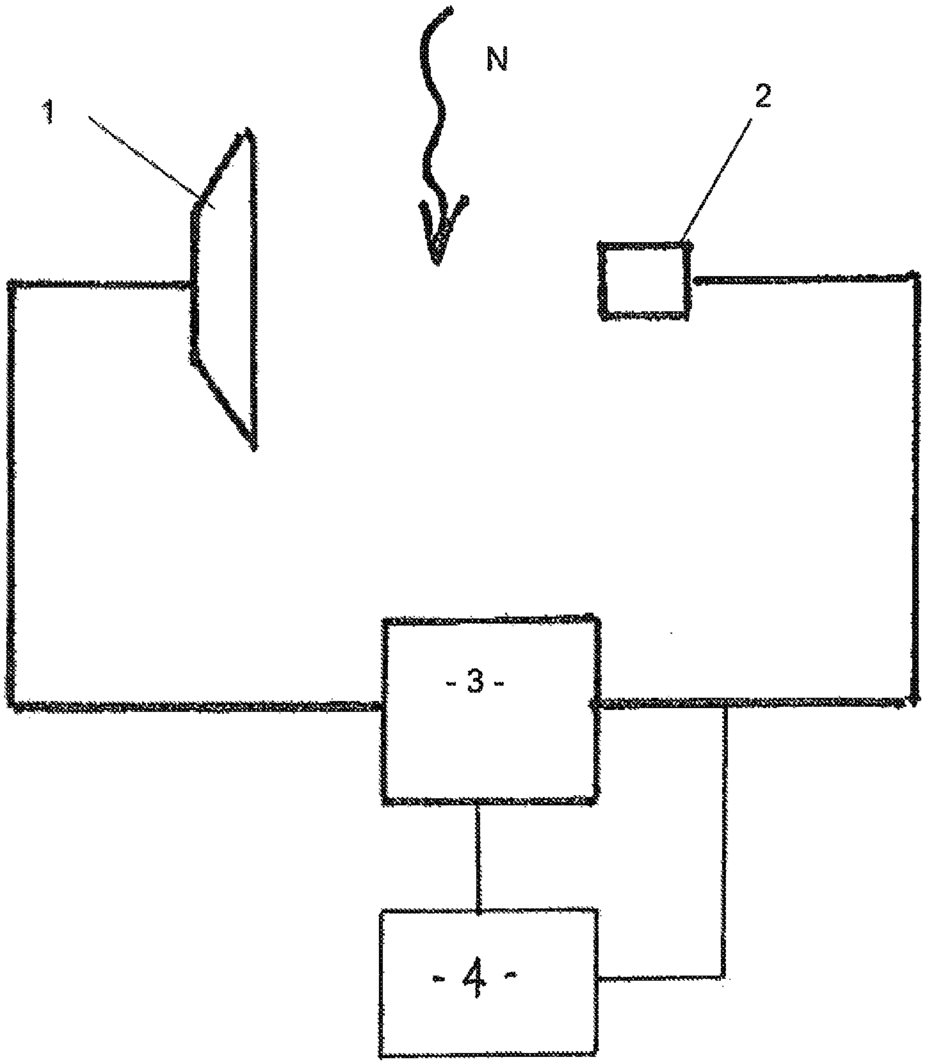

FIG. 4: Is a diagrammatic representation of a feedback active noise cancellation system according to one embodiment of the invention.

DESCRIPTION OF ONE OF MORE EMBODIMENTS

Referring to FIG. 1, a known active noise cancellation system is shown in which a speaker or driver 1 delivers sound in a selected region, usually the enclosed space between a headset or earphone and the user's inner ear, for example. The sound from loudspeaker 1 is sensed by sensing microphone(s) 2, which also senses any noise N in the selected region. A controller 3 receives the output from the sensing microphone(s) 2 and applies an appropriate control law to actuate the speaker 1 such that the noise N is effectively cancelled.

In order to provide an appropriate signal to speaker 1, the controller 3 must realise a suitable control law transfer function between the sensing microphone (s) and speaker.

Turning now to FIG. 2, a plot of gain against frequency for a control law transfer function known for use in the active noise cancellation system as broadly outlined in FIG. 1 is shown. As can be seen from FIG. 2, the general form of the function includes an amplitude peak at around 300 Hz, a notch at approximately 8 kHz, and a rising characteristic above 10 kHz.

In order to realise the function shown, a solution is proposed which uses a plurality of filters having one or more adjustable parameters. The filters are each operable over a different selected frequency range in a similar manner to a multi-channel audio equaliser. Thus the filters may cumulatively realise a required control law transfer function. In one embodiment, the proposed solution uses parametric filters, although those skilled in the art will appreciate that other forms of filter may be used. Those skilled in the art will also realise that the resultant circuit construction may take a variety of physical forms, and may in some embodiments be provided in the form of an integrated circuit with few, if any, additional components.

A parametric filter allows adjustment of centre frequency, quality factor (Q) and amplitude. Therefore, a parametric filter provides significant flexibility for an application such as the realisation of a selected frequency band of a control law transfer function.

Control law transfer functions are invariably based on a minimum phase system, and therefore the amplitude and phase characteristics are uniquely related. Accordingly, one only needs to realise the desired amplitude response and the phase response will automatically follow, or vice versa. Hence in some embodiments the adjustable parameter for one or more of the filters may simply be amplitude.

In one embodiment a plurality of parametric filters may be used together, in a manner similar to use of a parametric equaliser, to realise a control law transfer function. In particular, if there is a sufficient number of filters (for example being analogous to a parametric equaliser with a number of channels) and range of adjustment, any amplitude shape i.e. any gain profile with respect to frequency can be realised over a selected bandwidth and so it is possible to realise any desired or required control law transfer function. In some embodiments, multiple filter parameters of multiple filters are adjustable. In other embodiments, only a single parameter of a single filter of the plurality of filters may be adjustable.

In practice, it is usually necessary to rationalise the number of channels, i.e. the number of filters and the range of adjustment in order to minimise circuit complexity. However, if appropriate informed design choices are made, then because of the inherent flexibility of each parametric filter, a wide range of control law transfer functions can still be approximated to a sufficient level of accuracy.

Therefore, turning to the control law transfer function characteristic illustrated in FIG. 2, it will be seen that this may be sufficiently well matched with a filter arrangement that is analogous to a "2.5" channel parametric equaliser, i.e. two parametric filters and a shelving filter. The first and second channels correspond to two parametric filters that are fully featured and cover the 300 Hz peak at 8 KHz notch. The third channel corresponds to a shelving filter with a frequency and amplitude adjustment only (i.e. no Q).

The amplitude of a parametric equaliser is typically centred around 0 dB, so a separate adjustable gain stage is used to realise the final control or transfer function. In this example around 12 dB of gain is provided by this stage.

Turning now to FIG. 3, a typical circuit to realise the control or transfer function of FIG. 2 using the parametric equaliser approach is shown. In FIG. 3, the "ESRC" block provides the overall system gain, the 40 k potentiometers set the channel amplitude, the 1 k adjustable resistors set the channel Q (which determines the bandwidth over which the filter operates) for the peak and the notch, and the frequency of the shelf, the 100 k adjustable resistors set the channel frequency for the peak and the notch.

For integration into an integrated circuit it is typically necessary to have C2 and C3 as external components owing to the low corner frequencies that they realise. For the other capacitors it is possible to integrate them by rescaling (i.e. reducing the capacitor value and increasing the resistor values) whilst still meeting noise floor specifications. The integrated resistors can be realised by a number of means such as "switch cap" or "transconductance".

The external component count is therefore only two capacitors (per left or right channel). The adjustable resistor settings can be programmed into the integrated circuit as a one time programmable (OTP) setting.

In another embodiment one or more parameters of one or more of the filters is dynamically adjustable. Therefore, the adjustable resistor settings for the embodiment shown in FIG. 3 may be reprogrammable settings permitting dynamic adjustment or change of control law transfer functions. FIG. 4 shows a system according to an embodiment of the invention in which the control law transfer function is realised by a controller 3 incorporating a plurality of filters (such as the arrangement shown in FIG. 3), at least one of the filters having an adjustable parameter. The FIG. 4 embodiment includes a dynamic performance adjustment controller 4 which sensing the noise cancellation performance of the apparatus comprising the system by monitoring the noise signal detected by the sensing microphone 2 and sends the necessary signals or instructions to the controller 3 to dynamically adjust one or more adjustable parameters of one or more of the filters that realise the control law transfer function. In one embodiment the adjustment controller 4 includes a digital signal processor which periodically monitors the signal from noise sensing microphone 2 and determines which parameters of the controller 3 require adjustment. Appropriate output signals (either analog or digital) are generated and provided to the controller 3 to make the required adjustment. The sensing microphone signal can then be used again to determine whether the adjustment is successful, and to what extent further adjustment is required.

As mentioned above, the invention may be used in association with an active noise cancellation device such as an active noise cancelling headset or earphone. In some embodiments the filters may be part of the device. In others, the filters may be remotely associated with the device, for example being provided in a remote control module. It will be seen that the invention allows continual or periodic monitoring of one or more acoustic or electro-acoustic characteristics of the active noise cancelling device so that the filter(s) can be adjusted to realise a control law transfer function dependent on the determined characteristic(s).

Similarly, the invention allows a generic filter circuit to be used which can be adjusted for different models or forms of active noise cancelling device. Furthermore, the invention may allow each specific device produced from a production line to be tested for one or more acoustic or electro-acoustic characteristics, so that the control law transfer function for each specific device may be adjusted to optimise performance of that device to account for manufacturing tolerances.

From the foregoing it will be seen that a solution is proposed which addresses the major limitations of the classical analog realisation of a control law transfer function. In particular, the invention provides an adjustable transfer function that is amenable to integration with a low external part count.

Those skilled in the art to which the invention relates will appreciate that the invention offers an elegant and viable alternative to a digital control law transfer function realisation. A digital realisation has the disadvantages of requiring high speed, low latency analog to digital and digital to analog conversion as well as the digital signal processing elements. This all comes at a cost in terms of power consumption, noise floor and price amongst others.

Those skilled in the art will also appreciate that the invention may equally be employed on a digital platform.

The invention claimed is:

1. An active noise cancellation apparatus comprising:

a sensing microphone;

a speaker; and a peak filter, a notch filter, and a shelving filter, each filter being operable over a different frequency range, the center frequency of the frequency range of the notch filter being greater than the center frequency of the frequency range of the peak filter and less than the center frequency of the frequency range of the shelving filter, and at least one of the peak, notch, or shelving filters having at least one adjustable parameter whereby the at least one filter can be adjusted such that the peak, notch, and shelving filters cumulatively realise a required active noise cancellation control law transfer function; and wherein the speaker receives a signal comprising an output of the sensing microphone modified by the control law transfer function.

2. Apparatus as claimed in claim 1 wherein each of the peak, notch, and shelving filters includes at least one adjustable parameter.

3. Apparatus as claimed in claim 2 wherein the adjustable parameter is amplitude.

4. Apparatus as claimed in claim 2 wherein the adjustable parameter is bandwidth.

5. Apparatus as claimed in claim 2, wherein the Q of the peak filter and the notch filter is adjustable.

6. Apparatus as claimed in claim 1 wherein the peak filter and the notch filter comprise parametric filters.

7. Apparatus as claimed in claim 1 wherein the adjustable parameter is dynamically adjustable.

8. Apparatus as claimed in claim 7 further comprising an adjustment controller adapted to monitor a noise signal from the sensing microphone and to adjust the at least one adjustable parameter.

9. Apparatus as claimed in claim 8 wherein a plurality of parameters are adjustable, and the adjustment controller determines which parameter or parameters of one or more of the peak, notch, and shelving filters requires adjustment.

10. Apparatus as claimed in claim 9, wherein the adjustment controller comprises a digital signal processor.

11. Apparatus as claimed in claim 7 further comprising an adjustable gain stage.

12. Apparatus as claimed in claim 1, further comprising an adjustable gain stage.

13. Apparatus as claim in claim 1 wherein the peak, notch, and shelving filters are analog.

14. Apparatus as claim in claim 1 wherein the filters are configured in a cascaded arrangement of peak filter, notch filter, and shelving filter.

15. Apparatus as claimed in claim 1, wherein the signal modified by the control law transfer function is adapted to cancel the noise signal sensed by the microphone.

16. Apparatus as claimed in claim 1, wherein the peak filter and notch filter have centre frequencies of approximately 300 Hz and 8 kHz respectively.

17. Apparatus as claimed in claim 1, wherein the signal generated by the control law transfer function is adapted to cancel noise not generated by the speaker.

18. A method of active noise cancellation for apparatus including a speaker, a sensing microphone, a peak filter, a notch filter, and a shelving filter, each of the plurality of filters being operable over a different frequency range, the center frequency of the frequency range of the notch filter being greater than the center frequency of the frequency range of the peak filter and less than the center frequency of the frequency range of the shelving filter and at least one of the filters having at least one adjustable parameter whereby the at least one filter can be adjusted, the method comprising:

monitoring a noise signal detected by the sensing microphone;

using the monitored signal to determine the noise cancellation performance of the apparatus;

dynamically adjusting the adjustable parameter dependent on the determined performance such that the plurality of filters cumulatively realise a control law transfer function to implement active noise cancellation; and actuating the speaker with an output of the sensing microphone modified by the control law transfer function.

19. A method as claimed in claim 18, wherein a plurality of parameters are adjustable and the method includes determining which parameter or parameters of one or more of the plurality of filters requires adjustment.

20. A method as claimed in claim 18, further comprising adjusting the gain of the apparatus.

21. Method as claim in claim 18 wherein the peak, notch, and shelving filters are analog.

22. A method as claimed in claim 18, wherein the signal modified by the control law transfer function is adapted to cancel the noise signal sensed by the microphone.

23. Apparatus for realising an active noise cancellation control law transfer function between a sensing microphone and a speaker, the apparatus comprising a plurality of filters, each filter being operable over a different frequency range, at least one of the plurality of filters having at least one adjustable parameter whereby the at least one filter can be adjusted such that the plurality of filters cumulatively realise an active noise cancellation control law transfer function, and an adjustment controller operable to monitor an externally generated noise signal detected by the sensing microphone and to dynamically adjust the at least one adjustable parameter whereby the plurality of filters cumulatively realise a control law transfer function required to implement active noise cancellation.

24. Apparatus as claimed in claim 23, wherein a plurality of parameters are adjustable, and the adjustment controller determines which parameter or parameters of one or more of the plurality of filters requires adjustment.

25. Apparatus as claimed in claim 24, wherein the adjustment controller comprises a digital signal processor.

26. Apparatus as claimed in claim 24, further comprising an adjustable gain stage.

27. Apparatus as claimed in claim 23, wherein the signal modified by the control law transfer function is adapted to cancel the noise signal sensed by the microphone.

* * * * *